United States Patent

Ryazanov et al.

(10) Patent No.: US 8,604,163 B2
(45) Date of Patent: Dec. 10, 2013

(54) EEF2K ASSAYS FOR IDENTIFYING COMPOUNDS THAT INHIBIT EEF2K ACTIVITY

(71) Applicant: University of Medicine and Dentistry of New Jersey, Somerset, NJ (US)

(72) Inventors: Alexey G. Ryazanov, Princeton, NJ (US); Benjamin E. Turk, New Haven, CT (US)

(73) Assignee: Rutgers, The State University of New Jersey, New Bruswick, NJ (US)

( * ) Notice: Subject to any disclaimer, the term of this patent is extended or adjusted under 35 U.S.C. 154(b) by 0 days.

(21) Appl. No.: 13/735,253

(22) Filed: Jan. 7, 2013

(65) Prior Publication Data

US 2013/0131313 A1 May 23, 2013

Related U.S. Application Data

(62) Division of application No. 12/837,478, filed on Jul. 15, 2010, now Pat. No. 8,349,576.

(60) Provisional application No. 61/225,875, filed on Jul. 15, 2009.

(51) Int. Cl.
*C07K 7/08* (2006.01)
(52) U.S. Cl.
USPC .......................................................... 530/300
(58) Field of Classification Search
None
See application file for complete search history.

(56) References Cited

U.S. PATENT DOCUMENTS

| 4,004,016 A | 1/1977 | Yale et al. |
| 6,346,406 B1 | 2/2002 | Ryazanov et al. |
| 7,250,428 B2 | 7/2007 | Pifferi |
| 2003/0083470 A1 | 5/2003 | Jones |

FOREIGN PATENT DOCUMENTS

WO   WO-2006099181 A2   9/2006

*Primary Examiner* — Nashaat Nashed

(57) ABSTRACT

Assays for identifying novel compounds for inhibiting eEF2 kinase and consequence peptides employed therein.

1 Claim, No Drawings

EEF2K ASSAYS FOR IDENTIFYING COMPOUNDS THAT INHIBIT EEF2K ACTIVITY

CROSS-REFERENCE TO RELATED APPLICATIONS

This application is a Divisional of U.S. patent application Ser. No. 12/837,478, filed on Jul. 15, 2010, now U.S. Pat. No. 8,349,576, having an issue date of Jan. 8, 2013, which claims priority to U.S. Provisional Patent Application No. 61/225,875, filed on Jul. 15, 2009. The contents of the foregoing applications are hereby incorporated by reference their entireties.

STATEMENT OF GOVERNMENT SUPPORT

This invention was made with government support under Grant No. 5R21RR022859-02 awarded by the National Institutes of Health. The government has certain rights in the invention.

FIELD OF THE INVENTION

The present invention relates to assays for identifying novel compounds for inhibiting eEF2 kinase and consequence peptides employed therein. The present invention is also directed to kits for practicing the scope of the present invention.

BACKGROUND OF THE INVENTION

The enzyme Elongation Factor 2 Kinase (eEF2-K) belongs to a novel family of protein kinases, with prototypical member being Dictyostelium myosin heavy chain kinase A (MHCK A), which display no homology to conventional eukaryotic protein kinases. This protein kinase is highly specific to Elongation Factor 2 (eEF2) and is responsible for eEF2 phosphorylation. eEF2 promotes ribosomal translocation, the reaction that results in the movement of the ribosome along mRNA during translation. eEF2 was identified among the most prominently phosphorylated proteins in crude tissue and cell lysates. Importantly, it was found that phosphorylation of eEF2 arrests translation, suggesting that this may be a critical mechanism by which the rate of protein synthesis is regulated (Ryazanov, A. G. (1987). Ca2+/calmodulin-dependent phosphorylation of elongation factor 2. FEES Lett 214, 331-334; Ryazanov, A. G., Shestakova, E. A., and Natapov, P. G. (1988).)

The activity of this kinase is increased in different types of cancers and may be a valid target for anti-cancer treatment. For example, it has been reported that eEF2-K is overexpressed in breast cancer cell lines and tumors with little or no activity observed in normal breast tissue. Moreover, there is evidence indicating that the enzyme is activated in rat glioblastoma (Chang et al, (1995) Calmodulin-dependant protein kinases in rat glioblastoma, Cell Growth Diff.) The natural product rottlerin has been shown to inhibit growth of glioma cell lines by inhibiting eEF2-K. Parmer et al, (1997) Cell Growth Differ. Vol. 8, 327)).

This enzyme was also shown to have increased activity in human brains of individuals with AD (Li, X., Alafuzoff, I., Soininen, H., Winblad, B., and Pei, J. J. (2005) Levels of mTOR and its downstream targets 4E-BP1, eEF2, and eEF2 kinase in relationships with tau in Alzheimer's disease brain. FEBS J.272, 4211-4220) although the mechanism and relevance of the enzyme for such purposes was not clear. Accordingly, eEF2 kinase inhibitors could be used to modulate the pathophysiology of a number of disease states including brain cancer, breast cancer, ischemic heart disease, etc.

It was recently discovered that inactivation of a ubiquitous cellular enzyme eEF2 kinase can confer resistance to radiation by suppressing radiation-induced apoptosis. Mucosal damage, such as the damage to the intestine is a major dose-limiting event in radiation therapy and chemotherapy. Aspects of rapid cell turnover, distinct compartmentalization of damage, and known differentiation pathways of crypt cells in the murine and human intestine have been well studied. Treating such conditions have been the subject of an ongoing research. Various modalities, such as antioxidant therapy and inhibition of serotonin activity at the gastric level, have been suggested and employed in the art. However, there is still a need to mitigate side effects associated with drug and radiation therapy.

Until now all alpha kinase phosphorylation sites in protein substrates identified fall within the structural class of alpha helices (Drennan and Ryazanov, 2004). It has been unclear whether these kinases have primary sequence specificity dictated by residues that surround the site of phosphorylation, or whether substrate recognition is mediated principally by secondary structure. Accordingly, there is a need in the art to clarify this issue as a means for developing targeted active ingredients.

SUMMARY OF THE INVENTION

The shortcomings of the prior art are now addressed in the present invention to provide a screening assay that can ascertain the degree of inhibition of eEF2 kinase by a test agent. The present invention provides for methods of for an inventive assay that for identifying suitable compounds for inhibition of eEF2 kinase. The present disclosure also describes a novel mechanism of action of eEF2 kinase.

Another aspect of the present invention is directed to the consensus peptide substrate eEF2 kinase for phosphorylation by eEF2K. In at least another embodiment of the present invention a method of screening for activity of modulating agents in eEF2 kinase pathway is developed employing a consensus sequence for phosphorylation by eEF2K having a Lys or an Arg residue at the +3 position, and a basic residue or Ser or Thr at the +2 position.

DETAILED DESCRIPTION OF THE INVENTION

Definitions

As used herein, "about" will mean up to plus or minus 5% of the particular term.

NOM As used herein, "consisting essentially of" refers to variations in the amino acid sequence of the substrate that would not change the binding rate or extent of the substrate to eEF2K by more than about 5 fold.

The instant invention relates to consensus peptides having a suitable sequence for measuring the activity of eEF2K. In general a peptide substrates for eEF2K are defined based on sequence relative to a Thr residue that is the site of phosphorylation (the zero position). The Positions C-terminal to the phosphorylation site are identified as the "+" positions, and the positions N-terminal to the phosphorylation site are the "−" positions. For example, the position immediately C-terminal to the site of phosphorylation is the +1 position, and the position two residues C-terminal to the Thr is the +2 position.

In at least one aspect of the present invention, consensus sequences have been identified containing Lys or Arg (basic)

residue at the +3 position, either a basic residue or Ser or Thr at the +2 position, to be critical for phosphorylation by eEF2K. Accordingly, at least one aspect of the present invention provides for polypeptide/protein and eEF2K to be included in a cell or cell lysates, wherein the consensus sequence is denoted as set forth in SEQ ID Nos: 1 and 2, respectively.

In another aspect of the present invention, the consensus sequences contain residues Gln and Glu at the −2 position, charged and hydrophilic residues at the −1 position. In a more preferred embodiment the consensus sequence contain at least one of the amino acids Ala, Ser, Thr, Val, Ile, Leu, Gln or Glu at the +1 position, and basic residues at the +4 position. In another embodiment the preferred substrate is 90% identical to SEQ. ID. No. 1 or SEQ. ID. No. 2 and contains a minimum of 5 and a maximum of 35 amino acid residues. A preferred peptide substrate contains a minimum of 7 and a maximum of 18 amino acid residues and is 91, 92, 93, 94, 95, 96, 97, 98, or 99% identical to SEQ ID No.1 or 2. The most preferred substrate sequence is: Ac-RKKYKFNEDTERRRFL (SEQ ID. No. 1) and Ac-RKKYRIVWKSIFRRFL (SEQ. ID. 2) which provides at least an unexpected 5, 10, 15, 20, 25, 30 to 35, and preferably 30 to 35 fold increase in activity as compared to known substrates such as MU-H having RKKF-GESEKTKTKEFL (SEQ. ID. No. 3).

In another aspect of the present invention, methods of identifying eEF2K inhibitors and analogues thereof as potential therapeutic means. In at least one embodiment, eEF2K inhibitory compounds of the present invention may be identified using a high-throughput screening assay, such that the assay discussed herein. Specifically, eEF2K can be produced in large quantities by E. coil, or using any other suitable means known in the art.

At least one embodiment of the present invention is directed to screening suitable test agents for their activity against eEF2K. In another embodiment, suitable modulating compounds are identified by providing a consequence sequence to interact with eEF2 kinase to ascertain the decrease in phosphate transfer by the enzyme into the substrate. In yet another embodiment of the present invention, suitable modulating agents increase or decrease the binding between the substrate and the enzyme as compared to the binding in the absence of the test agent, wherein increased or decreased binding between the at least one protein or peptide and eEF2 kinase is indicative of a modulating agent eEF2 kinase pathway.

Phosphorylation of a consensus sequence, such as Ac-RKKYKFNEDTERRRFL (SEQ ID NO: 1), for eEF2K activity can be measured and compared with reduced activity seen in the presence of a test compound. In one non-limiting embodiment, kinase activity is measured in both control and test batches based on the depletion of ATP. In another aspect of the present invention, active eEF2K utilizes ATP when phosphorlyating the consensus sequence. Thus, a reduction in ATP signals an active kinase.

In a preferred embodiment, the reduction in ATP signals is visually detected and quantified by coupling the reaction with a luciferase luminescence assay, which is ATP dependent. Thus, active kinase will reduce ATP and, thereby, reduce the luminescence detected. Conversely, inhibition of eEF2K by a test compound prevents depletion of ATP, which is detected as an increased luminescence.

In at least another embodiment of the present claims screening kits for determining the activity of eEF2 kinase inhibitors are contemplated wherein the kit contains the at least one protein or peptide having a consensus sequence for phosphorylation by eEF2K comprising a Lys or Arg residue at the +3 position, and a basic residue or Ser or Thr at the +2 position with eEF2 kinase, preferably those set forth in SEQ ID NO. 1 or 2 or at least those having 95 to 99% identical peptide chain, and a phosphate source, other suitable reagents and direction of use.

Without seeking to limit the possible scope of use of the identified compounds are envisioned to be use as a treatment regimen for targeting the inhibition of eEF2K phophorylative activity. Such treatment regimens may include treatment of Alzheimer's Disease or induction of Long Term Potentiation of Synaptic Transmissions. Result below also suggest that eEF2K can be an important component of the apoptotic pathway, and its inactivation can confer resistance to radiation. Accordingly, selective inhibitors of eEF2K can be used as drugs to protect tissues from cell death caused by radiation.

Another aspect of the present invention is directed methodologies for identifying said compound that employs both the consensus peptide substrates and a high-trough assay.

EXAMPLES

Example 1

Discovery of Consensus Peptide Substrates for eEF2K

To determine whether eEF2K is sequence specific, we made use of an arrayed peptide library approach, (Turk Lab, Beth Israel Deaconess Medical Center Dept. of Pharmacology), that systematically evaluates the preference of a given kinase for every amino acid at each of nine positions surrounding the phosphorylation site (Hutti et al., 2004).

The method employed a library of roughly 200 distinct peptide mixtures. Each peptide contains a central fixed phosphorylation site (an equimolar mixture of serine and threonine) flanked on either side by degenerate positions, and a carboxy-terminal biotin tag. For each of nine positions surrounding the phosphoacceptor site, twenty-two peptide mixtures are made in which each of the twenty unmodified proteogenic amino acids as well as phosphothreonine and phospho-tyrosine are fixed. The entire collection thus consists of 198 (22×9) peptides. These peptide substrates are arrayed in a spatially addressable manner in a 384-well plate and treated with the kinase of interest and radiolabeled ATP. Control reactions are also run in the absence of peptide to determine the background from kinase alone. At the end of the incubation time, aliquots of each reaction are spotted simultaneously onto a streptavidin membrane using a capillary pin-based liquid transfer device. The membrane is immersed in a quenching solution, washed extensively to remove unincorporated label, dried, and exposed to a phosphor screen. This allows the amount radiolabel incorporated into peptide to be quantified, providing an indication of which peptides are the most efficient substrates for a particular kinase. This in turn indicates which amino acids at a particular position influence phosphorylation by that kinase.

The inventors of the present invention performed initial runs using the peptide library with eEF2K. The kinase was able to efficiently phosphorylate peptides within the library, and displayed significant amino acid preferences at several positions. eEF2K is highly selective for basic residues at the +3 position, with a secondary preference for basic and possibly serine/threonine at the +2 position. The eEF2K phosphorylation motif bears little resemblance to any of the motifs ascribed to conventional protein kinases (Pinna and Ruzzene, 1996). For example, no previously characterized kinases have principal selectivity for basic residues at the +3 position as seen with eEF2K.

Using information from peptide screening, the inventors generated the consensus peptide substrate called eEF2p, bearing a consensus sequence for phosphorylation by eEF2K (with the sequence Ac-RKKYKFNEDTERRRFL, SEQ ID. No. 1). For comparative purposes an additional peptide TRPM7p (Ac-RKKYRIVWKSIFRRFL, SEQ. ID. No. 2) was prepared, bearing a consensus sequence for phosphorylation by another α-kinase, TRPM7 kinase.

In reactions performed at a single substrate concentration (100 μM), it was found that both peptides are efficiently phosphorylated by their respective kinases. These new peptides are significantly better substrates for their kinases and show an unexpected 30 to 35 fold increase in activity as compared to previously identified peptide MH-U used in the art to assay for eEF2 kinase. These preliminary results indicate that the present inventors have been able to generate a highly efficient eEF2 kinase substrate that will form the basis for our investigations of the kinetic mechanism and mode of substrate recognition for this kinase.

Example 2

Development of High-Throughput Screening Assay

Using the obtained peptide substrate (eEF2p) the present inventors then developed a high-throughput screening assay to identify small molecule inhibitors of eEF2K. Accordingly a biochemical assay of eEF2K in order to avoid problems associated with cell toxicity was pursued, as well as, the inhibition of targets other than eEF2K. The latter problem could be acute for a cell-based assay, because signal transduction pathways including eEF2K are not clearly defined and therefore unknown components could be inhibited in the assay. eEF2K expressed in high yield in *E. coli* is a good source of the enzyme for these studies, because it has a high activity and it is also stable (Pavur et al., 2000).

A screen using eEF2K peptide substrate was employed based on the depletion of ATP (Kupcho et al., 2003; Singh et al., 2004). In the next step, a coupled luminescent assay using luciferase, an ATP-dependent enzyme was performed. In this scenario, a decrease in ATP concentrations or levels over the course of the reaction result in less luciferase activity. Kinase inhibition is thereby measured as an increase in luminescence.

Example 3 eEF2K Inhibitor Screening

To identify novel eEF2 kinase inhibitors, the inventors have screened 10,000 compounds from ChemBridge using the developed high-throughput methodology. For high-throughput eEF2k inhibitors screening assay, GST-tagged human eEF2k is expressed and purified from *E. coli* expression system, and specifically designed short peptides mimicking eEF2 are synthesized and used as substrates. Master Mix (166.67 mM pH 6.6 HEPES-KOH, 666.67 μM α-peptide, 0.2 U/μL Calmodulin, 16.67 mM DTT, 333.33 μM $CaCl_2$, 33.33 mM $MgCl_2$) was prepared to achieve the optimal kinase activities. To start the kinase assay, A 10 minute incubation of 1 uL eEF2k, 100 μM small molecular compounds and 3 uL Master Mix were first done at room temperature in 96-well plates. After that, 10 μM ATP was added to each well to continue another 30 minutes incubation at the 30° C. incubator. Finally, Kinase Glo Luminescet Kinase Assay Platform was used to stop reactions and generate luminescence as readout by quantifying the amount of ATP left in solutions. Because inhibition of eEF2k activity will block its usage of ATP, the compounds with higher readouts will be selected as candidates for further experiments.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and script of the invention, and all such variations are intended to be included within the scope of the following claims.

The invention claimed is:

1. The peptide substrate of TRPM7 comprising Ac-RKKYRIVWKSIFRRFL (SEQ. ID. NO: 2).

* * * * *

SEQUENCE LISTING

```
<160> NUMBER OF SEQ ID NOS: 3

<210> SEQ ID NO 1
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 1

Arg Lys Lys Tyr Lys Phe Asn Glu Asp Thr Glu Arg Arg Arg Phe Leu
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Synthetic Peptide
```

```
<400> SEQUENCE: 2

Arg Lys Lys Tyr Arg Ile Val Trp Lys Ser Ile Phe Arg Arg Phe Leu
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 3

Arg Lys Lys Phe Gly Glu Ser Glu Lys Thr Lys Thr Lys Glu Phe Leu
1               5                   10                  15
```